United States Patent [19]

Braun

[11] Patent Number: 5,366,078
[45] Date of Patent: Nov. 22, 1994

[54] VENTED CARRYING CASE FOR CONTACT LENSES

[75] Inventor: Alan J. Braun, Livonia, N.Y.

[73] Assignee: Bausch & Lomb Incorporated, Rochester, N.Y.

[21] Appl. No.: 127,937

[22] Filed: Sep. 28, 1993

[51] Int. Cl.⁵ .............................................. B08B 3/04
[52] U.S. Cl. ..................................... 206/5.1; 134/901; 422/113; 422/301
[58] Field of Search ......................... 134/901; 206/5.1; 422/113, 297, 300, 301

[56] References Cited

U.S. PATENT DOCUMENTS

| | | | |
|---|---|---|---|
| 4,396,583 | 8/1983 | LeBoeuf | 134/901 X |
| 4,637,919 | 1/1987 | Ryder et al. | 422/300 |
| 4,750,610 | 6/1988 | Ryder | 134/901 X |
| 4,889,693 | 12/1989 | Su et al. | 134/901 X |
| 5,143,104 | 9/1992 | Iba et al. | 134/901 X |
| 5,196,174 | 3/1993 | Cerola et al. | 422/300 |
| 5,250,266 | 10/1993 | Kanner | 134/901 X |
| 5,270,002 | 12/1993 | Neff, II et al. | 134/901 X |

Primary Examiner—Philip R. Coe
Attorney, Agent, or Firm—Craig E. Larson

[57] ABSTRACT

A case for disinfecting, cleaning or storing contact lenses is described that provides a venting system for discharging gas therefrom without significant liquid discharge. The case includes a cap securable to a container, having an inner surface including a hollow pedestal with its open distal end extending into the container. The end of the pedestal adjacent the inner cap surface encompasses an aperture through said cap for venting and discharging of gas to the environment. A gas and liquid impermeable gasket fits inside the hollow end of the pedestal adjacent the aperture area, permitting venting of gas but not liquid through the adjacent aperture. A support for holding and positioning contact lenses in the container includes a post that is fitted into the distal end of the hollow pedestal, wherein the pedestal and post are provided with a channel therethrough to permit gas to escape from the container through the gasket and adjacent aperture.

9 Claims, 2 Drawing Sheets

VENTED CARRYING CASE FOR CONTACT LENSES

BACKGROUND OF THE INVENTION

The present invention relates to a vented case for holding contact lenses that is capable of venting gases from the case interior as chemical reactions proceed therein during disinfecting, cleaning or storing of the lenses in contact with a treating solution. More particularly, the invention relates to a contact lens case that is capable of adequately venting oxygen from said case during neutralization of a hydrogen peroxide disinfecting solution.

Maintenance of contact lenses typically requires immersion in various cleaning, disinfecting or storage solutions. A number of maintenance processes involve chemical reactions which may involve the generation of gaseous by-products. For example, contact lenses are conventionally disinfected by contacting them with a dilute solution of hydrogen peroxide. At the completion of the disinfecting process lenses must be freed of any residual hydrogen peroxide. A number of regimens for this purpose involve catalytic decomposition of the hydrogen peroxide with evolution of oxygen. The agent for decomposing the hydrogen peroxide may be a metal catalyst or an enzyme such as catalase. The hydrogen peroxide disinfecting solution must typically contact the decomposing or neutralizing agent for a significant period of time to completely decompose the hydrogen peroxide. Thus, the container holding the lenses and solution is preferably continuously vented to permit the gases to vent from the container to the environment rather than risk fracture or rupture of the container through buildup of excessive gas pressure. A number of prior workers describe various systems and mechanisms for releasing and venting gas pressure from lens cases.

Iba et al in U.S. Pat. No. 5,143,104 describe a vented lens case in which gas vents through a rather complexly formed grooved and multiple aperture cap in combination with an impermeable membrane that includes an H-shaped perforation that acts as a one-way valve to vent gas while preventing liquid from discharging from the container. Su et al in U.S. Pat. No. 4,889,693 describe a deformable plug that functions as a one-way valve when pressure in the case sufficiently deforms the plug.

In U.S. Pat. No. 4,637,919, Ryder et al describe a vented case, again of a rather complex nature, that includes an apertured cap fitted with a plug that includes a semi-permeable membrane for ventage. In LaBoeuf U.S. Pat. No. 4,396,583, a vented case is described having a cap including a cavity for supporting a vapor-permeable, liquid-impermeable barrier through which gas is vented.

Each of the prior systems involves relatively complex structures, increasing the costs of the device, as well as adding to the difficulty of manufacture. In addition, many of the prior art cases leak when upset. It is desirable to provide a simplified venting system, yet provide effective venting of gas without significant discharge of fluid, particularly, for example, if the case should be upset during transport.

SUMMARY OF THE INVENTION

The invention is a case or vial container for disinfecting, cleaning or storing of contact lenses in a solution wherein the case is vented for discharge of gases generated internally during a chemical reaction of interest, without significant discharge of fluid. The case includes a container having side walls, a bottom and an open top, typically cylindrical in shape, preferably with an expanded upper portion to accommodate separation of gas and liquid. The case is provided with a removable, sealable cap fitted, preferably threaded, to the open top of the container. The cap inner surface includes a hollow pedestal with a distal open end extending into the container wherein the end adjacent to said inner cap surface encompasses an aperture venting the cap to the environment.

A gasket of gas and liquid impermeable material is fitted inside the hollow end of the pedestal and positioned adjacent to the cap aperture, wherein the gasket, preferably including one or more apertures, permits venting of gas but not liquid through the cap aperture. A support for holding and positioning contact lenses in the container in contact with the treating solution is provided, comprising a post that is fitted into the distal end of the hollow pedestal. A notch in the distal end of the pedestal aligned with a channel formed in the post cross sectional structure permits venting of the gas from the container through the cap vent.

Alternatively, the impermeable gasket may be smaller in diameter than the hollow pedestal, forming a "loose fit" wherein the gasket acts as a valve permitting discharge of gas but not significant liquid through the cap aperture. In another embodiment, the gasket fits snugly in the hollow pedestal adjacent the cap venting aperture and includes a notch in its outer periphery wherein gas but not significant liquid vents through the cap aperture.

DETAILED DESCRIPTION OF THE INVENTION

Figure 2:
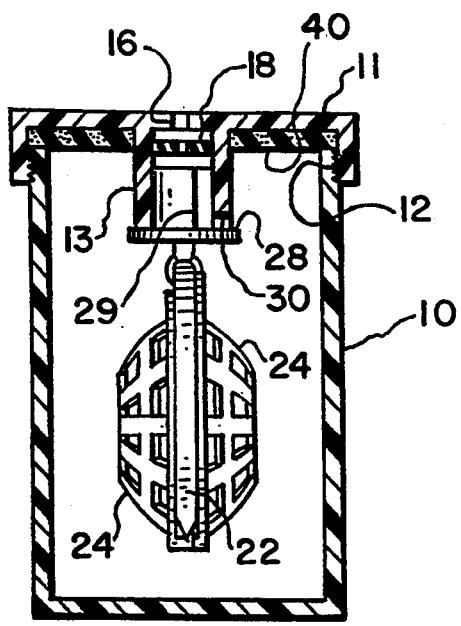
FIG. 2 is a partial sectional elevational view of the lens case of FIG. 1.
Figure 1:
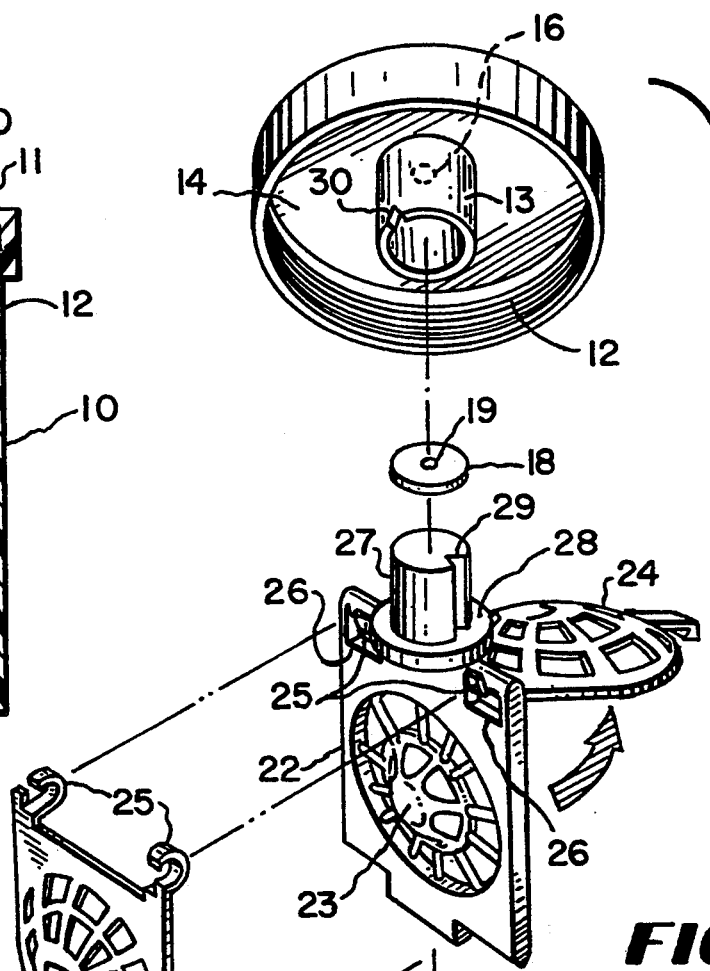
FIG. 1 is an exploded perspective view of the vented lens case of the invention.
Figure 1:
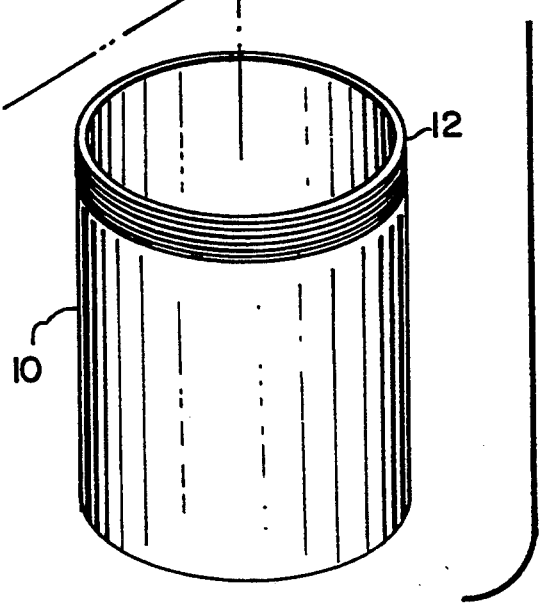

Referring to FIGS. 1 and 2, the vented case of the invention includes a container 10 that is of sufficient capacity to submerge a pair of contact lenses in a desired liquid chemical treating solution, such as a disinfecting solution of hydrogen peroxide. A cap 11 is fitted to the container by means of threads 12. A gasket 40 provides a seal between the cap and container. A hollow pedestal 13 is fixed to (or is formed as an integrally molded feature of the cap) and centered on the inner surface 14 of the cap with the end of the hollow pedestal adjacent the inner surface 14 encompassing an aperture 16 that penetrates the cap and is of sufficient dimensions to permit discharge of gas generated during the chemical reaction of interest, here, the decomposition of residual hydrogen peroxide. The distal end 17 of the pedestal extends into the container 10.

A hydrophobic, impermeable gasket 18 is sealingly fitted into the hollow pedestal adjacent to the aperture 16 and is designed to permit continuous discharge of gas from the container while preventing significant discharge of fluid therefrom. In a preferred embodiment, shown in FIG. 1, the gasket 18 fits snugly into the hollow pedestal and is provided with an aperture 19 that is of sufficient dimension to discharge gas at a satisfactory rate such that excessive pressure does not build up in the case. The aperture 19 is small enough so that there is no significant discharge of liquid from the system even when the case is inverted or lies horizontally. A preferred material of construction of said gasket is a hydrophobic silicon such as Dow Corning Product No. 20775-$^G$. A preferred gasket 18 is 0,300 inches in outer diameter with a central aperture of 0.011 inches in diameter.

A supporting structure 22 holds and positions contact lenses properly submerged in the treating solution in container 10. It is of conventional design, including convex surfaces 23 on which the lenses rest such as they are exposed to the treating solution. A pair of baskets 24 secure the lenses in place during treating and are pivotably mounted means of a pair of hinges 25 fitted about bearing surfaces 26 on the support 22.

Figure 4:
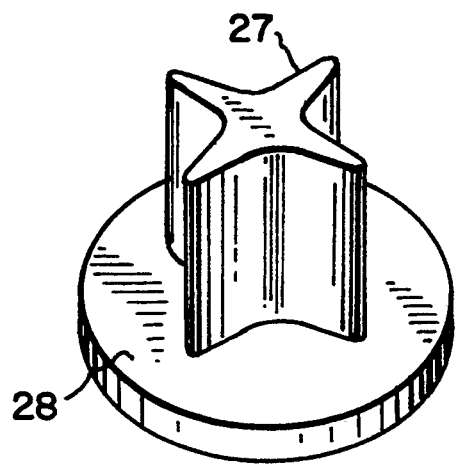
FIG. 4 is a perspective view of an alternative embodiment of the mounting post shown in FIGS. 1 and 2.
Figure 5:
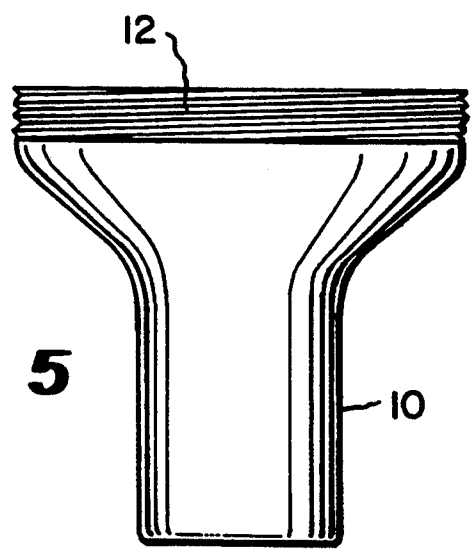
FIG. 5 is a front view of an alternative embodiment of the container shown in FIGS. 1 and 2.

The lens support structure 22 includes a mounting post 27 for fixing the structure to the cap by means of insertion into the distal hollow end of the pedestal 13. A stop 28 limits the depth the post is advanced into the pedestal such that the gasket 18 is provided with desired clearances. The mounting post is formed such that a channel is provided for gas to escape from the container. In the preferred embodiment of FIG. 1, a channel 29 in the post accommodates gas discharge. A notch 30 in the pedestal 13 aligns and registers with the post channel 20 to complete the gas discharge channel. Alternatively, as illustrated in FIG. 4, the post may be formed into an X-shape in cross section to accommodate gas discharge when the pedestal notch is aligned with the channel formed between the arms of the X.

Figure 3:
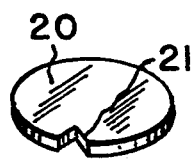
FIG. 3 is a perspective view of an alternative impermeable gasket of the invention.
Figure 6:
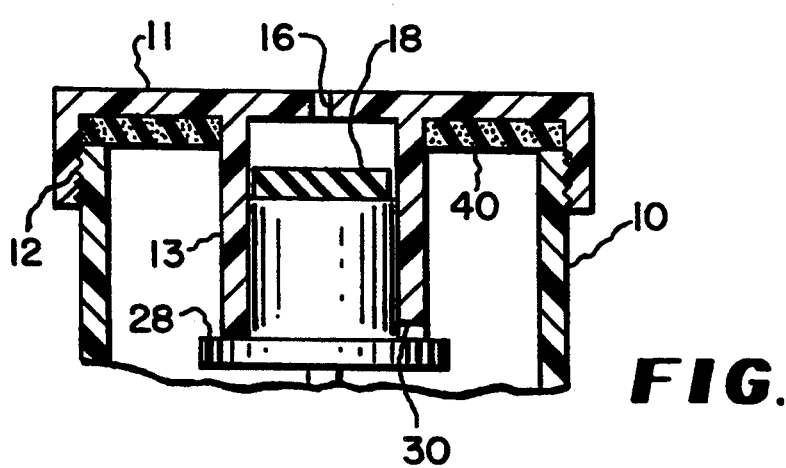
FIG. 6 is an enlarged partial sectional view of the vented lens case showing an alternative impermeable gasket of the invention.

In another embodiment of the invention, a gasket 20, shown in FIG. 3, is provided with a notch 2t of appropriate dimensions cut into the periphery thereof. A third embodiment illustrated in FIG. 6, requires that the diameter of the gasket to be slightly reduced to provide a "slack fit" of sufficient dimensions within the hollow pedestal to allow gas to by-pass the gasket yet still prevent discharge of significant amounts of liquid.

What is claimed:

1. A case for disinfecting, cleaning or storing contact lenses, wherein said case is vented, comprising;
   a container having side walls, a bottom wall and an open top;
   a removable, sealable cap, fitted to the open top of the container, said cap having an inner surface including a hollow pedestal having an end adjacent said inner cap surface that encompasses an aperture venting said cap to the environment and a distal open end that extends into the container;
   a gas and liquid impermeable gasket fitted inside the hollow end of the pedestal adjacent the encompassed aperture of the cap, wherein said gasket permits venting of gas but not liquid through said adjacent cap aperture; and
   a support for holding and positioning contact lenses in said container, said support comprising a post that is fitted into the distal end of the hollow pedestal, said pedestal and post including a channel permitting venting of gas from the container interior through the cap aperture.

2. The case of claim 1 wherein said gasket is provided with one or more apertures through which gas but not significant liquid from said case escapes and then vents through said cap aperture.

3. The case of claim 2 wherein said gasket is provided with a single, substantially centrally located aperture.

4. The case of claim 1 wherein said gasket is notched in its outer periphery through which gas but not significant liquid escapes from said case through said cap aperture.

5. The case of claim 1 wherein said gasket is smaller in diameter than said pedestal, forming a loose fit therein through which gas but not significant liquid escapes from said case through said cap aperture.

6. The case of claim 1 wherein the channel permitting discharge of gas from the case interior past the pedestal and supporting post includes a notch in the distal end of said pedestal and the supporting post comprises a cross section that includes a groove, wherein said notch and groove align to permit escape of gas from the container through the container top aperture.

7. The case of claim 6 wherein said contact lens supporting post is X-shaped in cross section, wherein alignment between arms of said X and said pedestal notch provide said channel for escape of gas from said container.

8. The case of claim 1, wherein the support for holding contact lenses, comprises:
   a center member extending from said post including projecting lens-shaped surfaces for receiving said contact lenses; and
   a pair of basket retainers, pivotably mounted upon said center member, for securing said lenses adjacent said surfaces.

9. The case of claim 1 wherein said container comprises an open top portion that flares outwardly to provide a gas-liquid separation zone to promote discharge of gas from the container without significant liquid content.

* * * * *

UNITED STATES PATENT AND TRADEMARK OFFICE
CERTIFICATE OF CORRECTION

PATENT NO. : 5,366,078
DATED : November 22, 1994
INVENTOR(S) : Alan J. Braun

It is certified that error appears in the above-indentified patent and that said Letters Patent is hereby corrected as shown below:

In column 3, line 24, after "mounted" insert -- by --.

In column 3, line 42, change "2t" to -- 21 --.

Signed and Sealed this

Eleventh Day of April, 1995

Attest:

BRUCE LEHMAN

*Attesting Officer*        *Commissioner of Patents and Trademarks*